(12) United States Patent
Van Rens et al.

(10) Patent No.: US 9,503,250 B2
(45) Date of Patent: Nov. 22, 2016

(54) DATA COMMUNICATION WITH INTERVENTIONAL INSTRUMENTS

(71) Applicant: KONINKLIJKE PHILIPS N.V., Eindhoven (NL)

(72) Inventors: Antonia Cornelia Van Rens, Nuenen (NL); Neil Francis Joye, Eindhoven (NL); Bout Marcelis, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 60 days.

(21) Appl. No.: 14/362,650

(22) PCT Filed: Oct. 25, 2012

(86) PCT No.: PCT/IB2012/055877
§ 371 (c)(1),
(2) Date: Jun. 4, 2014

(87) PCT Pub. No.: WO2013/061272
PCT Pub. Date: May 2, 2013

(65) Prior Publication Data
US 2014/0336623 A1 Nov. 13, 2014

Related U.S. Application Data

(60) Provisional application No. 61/552,627, filed on Oct. 28, 2011.

(51) Int. Cl.
*H04L 7/00* (2006.01)
*H04L 7/02* (2006.01)
(Continued)

(52) U.S. Cl.
CPC ............ *H04L 7/0008* (2013.01); *A61M 25/00* (2013.01); *A61M 25/09* (2013.01); *H04L 7/02* (2013.01); *H04L 67/12* (2013.01); *A61B 5/0013* (2013.01); *A61M 2205/3576* (2013.01)

(58) Field of Classification Search
CPC ... H04L 7/033; H04L 7/027; H04L 25/4904; H04L 7/0331; H04L 7/0337; H04L 7/0338; G11B 20/1403; H03L 7/0814

USPC ........ 375/219-221, 242-254, 259, 309-315, 375/353-376
See application file for complete search history.

(56) References Cited

U.S. PATENT DOCUMENTS 4,681,111 A 7/1987 Silvian
4,888,764 A * 12/1989 Haug ...................... H04L 12/40
375/219

(Continued)

FOREIGN PATENT DOCUMENTS

| EP | 0889616 | 1/1999 |
|---|---|---|
| EP | 2158841 | 3/2010 |
| WO | WO2010097111 | 9/2010 |

OTHER PUBLICATIONS

J. Ji et al., "An Ultraminiature CMOS Pressure Sensor for a Multiplexed Cardiovascular Catheter", IEEE Transactions on Electron Devices, vol. 39, No. 10, Oct. 1992, pp. 2260-2267.

*Primary Examiner* — James M Perez (57) ABSTRACT

The invention relates to a data communication system (100) and a method that can particularly be applied for communicating data from a medical instrument like a catheter or a guide-wire via a high-speedlink (101). The system (100) comprises (in-vivo) a slave component (150) with a controllable slave clock (153) and a transmitter (151) for transmitting a data signal (ds) that is clocked by the slave clock signal (clk). Moreover, it comprises (ex-vivo) a master component (110) with a clock controller (114,115,116) that receives a master clock signal (ref_clk) and the data signal (ds) and that generates a clock control signal (ccs) for adjusting the slave clock (153) to the master clock (113). The slave clock (153) may thus be realized with low space and energy requirements, e.g. by a voltage controlled oscillator (VCO). Moreover, the link (101) via which the data signal (ds) and the clock control signal (ccs) are exchanged may be realized by just two signal wires.

13 Claims, 5 Drawing Sheets

(51) Int. Cl.
*A61M 25/00* (2006.01)
*A61M 25/09* (2006.01)
*H04L 29/08* (2006.01)
*A61B 5/00* (2006.01)

(56) References Cited

U.S. PATENT DOCUMENTS

| | | | | |
|---|---|---|---|---|
| 4,987,374 | A * | 1/1991 | Burke | 329/302 |
| 5,399,965 | A * | 3/1995 | Heberle | H04L 25/0266 324/117 H |
| 5,437,060 | A * | 7/1995 | Delamater | H04B 15/04 375/357 |
| 5,608,357 | A * | 3/1997 | Ta | H03K 3/03 331/173 |
| 6,107,948 | A * | 8/2000 | Scott | H04B 14/062 341/143 |
| 6,319,208 | B1 | 11/2001 | Abita et al. | |
| 6,539,316 | B1 * | 3/2003 | Doten | A61B 8/06 702/33 |
| 6,922,436 | B1 * | 7/2005 | Porat | H03M 1/66 375/222 |
| 2002/0150116 | A1 * | 10/2002 | Huang | H04B 3/548 370/431 |
| 2003/0035503 | A1 * | 2/2003 | Sanduleanu | H03L 7/07 375/376 |
| 2004/0059396 | A1 * | 3/2004 | Reinke | A61N 1/372 607/60 |
| 2004/0122490 | A1 * | 6/2004 | Reinke | A61N 1/025 607/60 |
| 2004/0155687 | A1 * | 8/2004 | Lee | H03K 3/3562 327/165 |
| 2004/0196926 | A1 * | 10/2004 | Chien | H04L 7/042 375/316 |
| 2005/0093854 | A1 * | 5/2005 | Kennedy | G06F 3/1423 345/213 |
| 2005/0110515 | A1 * | 5/2005 | Ju | G01R 19/0053 326/14 |
| 2005/0197680 | A1 | 9/2005 | DelMain et al. | |
| 2005/0203392 | A1 * | 9/2005 | Petersen | G01S 15/8927 600/437 |
| 2005/0261569 | A1 * | 11/2005 | Schulz | G01R 33/285 600/411 |
| 2007/0023888 | A1 * | 2/2007 | Fujii | H01L 21/76898 257/698 |
| 2009/0015304 | A1 * | 1/2009 | Yin | H03L 7/06 327/162 |
| 2009/0062880 | A1 * | 3/2009 | Li | A61N 1/37288 607/32 |
| 2010/0204766 | A1 | 8/2010 | Zdeblick et al. | |
| 2010/0283532 | A1 * | 11/2010 | Horan | G09G 5/003 327/530 |
| 2010/0283894 | A1 * | 11/2010 | Horan | H04L 25/02 348/441 |
| 2011/0012648 | A1 * | 1/2011 | Qiao | H03B 19/00 327/141 |
| 2011/0034964 | A1 | 2/2011 | Bi et al. | |
| 2011/0038429 | A1 * | 2/2011 | Sako | H01Q 1/242 375/259 |
| 2011/0142112 | A1 * | 6/2011 | Lin | H04L 7/0008 375/224 |
| 2011/0213220 | A1 * | 9/2011 | Samuelsson | A61B 5/6851 600/301 |
| 2011/0293041 | A1 * | 12/2011 | Luo | H04L 5/20 375/316 |
| 2012/0087452 | A1 * | 4/2012 | Zerbe | H04L 25/0264 375/354 |
| 2012/0126612 | A1 * | 5/2012 | Hurwitz | H04B 3/54 307/3 |
| 2013/0034197 | A1 * | 2/2013 | Aweya | H04J 3/0664 375/362 |
| 2015/0188697 | A1 * | 7/2015 | Lin | H03L 7/085 375/375 |

* cited by examiner

DATA COMMUNICATION WITH INTERVENTIONAL INSTRUMENTS

CROSS-REFERENCE TO PRIOR APPLICATIONS

This application is the U.S. National Phase application under 35 U.S.C. §371 of International Application Serial No. PCT/IB2012/055877, filed on Oct. 25, 2012, which claims the benefit of U.S. Application Ser. No. 61/552,627, filed on Oct. 28, 2011. These applications are hereby incorporated by reference herein.

FIELD OF THE INVENTION

The invention relates to a data communication system and a method for communicating a data signal. Moreover, it relates to components of the data communication system, to a medical instrument, particularly a catheter or a guide-wire, and to a medical system.

BACKGROUND OF THE INVENTION

Instruments used in medical interventions like minimal invasive surgery are increasingly equipped with one or more sensors that transmit data from inside the body. A cardiovascular catheter has for example been described that comprises a pressure sensor, wherein an external clock signal is provided to this sensor to allow for a digital data communication (Jin Ji et al., "An Ultraminature CMOS Pressure sensor for a multiplexed cardiovascular catheter", IEEE transactions on electron devices, Vol. 39, No. 10, Oct. 1992).

SUMMARY OF THE INVENTION

It is an object of the present invention to provide means that allow for a high-speed data communication, particularly a communication between an interventional instrument and external equipment, wherein the components inside the instrument shall preferably have low space and/or energy demands.

This object is achieved by a data communication system according to claim 1, a method according to claim 2, a slave component according to claim 11, a master component according to claim 12, a medical instrument according to claim 13, and a medical system according to claim 14. Preferred embodiments are disclosed in the dependent claims.

A data communication system according to the present invention serves for the communication or transfer of data from one communication partner to another. It comprises the following components:

a) A first component, called "slave component" (or briefly "slave") in the following to indicate that it is the subject of a higher level control of the communication system. The slave component shall comprise the following subcomponents:

a1) A clock for generating a clock signal, wherein these elements will in the following be called "slave clock" and "slave clock signal" for purposes of reference. The slave clock shall be controllable, which means that a characteristic parameter of the slave clock signal (typically its frequency) can be adjusted within given limits.

a2) A transmitter for transmitting a data signal that is clocked by the slave clock signal. This means that the data signal will "embed" at least a part of the slave clock signal and have a direct relation thereto (such that the clock signal can at least partially be retrieved from the data signal). This is preferably achieved with a digital data signal, in which the sequence of data bits may for example be synchronized with the slave clock signal. Analog data signals are however possible, too, for example by use of amplitude modulation or multilevel signaling.

The data that are encoded in this data signal are assumed to be provided by another (logical) component than the slave component, for example by one or more sensors (which are functionally not a part of the communication system, though they may e.g. be realized on the same ASIC device).

b) A second component, called "master component" in the following, which comprises the following subcomponents:

b1) A receiver for receiving the above mentioned data signal.

b2) A clock for generating a clock signal, wherein these elements will in the following be called "master clock" and "master clock signal" for purposes of reference.

b3) A clock controller that receives the aforementioned master clock signal and the received data signal and that generates a "clock control signal" by which the slave clock can be adjusted to the master clock. This adjustment means that at least one characteristic parameter of the slave clock signal is altered to optimally match a given target parameter provided by the master clock signal. As a typical example, the frequency of the slave clock signal may be adjusted to the frequency of the master clock signal.

c) A link or communication channel via which the above mentioned data signal and the clock control signal can be exchanged between the slave component and the master component. Via this link, the transmitter of the slave component is hence coupled to the receiver of the master component, and the clock controller of the master component is coupled to the slave clock of the slave component.

According to a second aspect, the invention relates to a method for transmitting a data signal via a link from a slave component to a master component, said method comprising the following steps:

a) Clocking the data signal with a slave clock signal that is generated by a slave clock in the slave component.

b) Receiving said data signal in the master component.

c) Recovering at least partially the slave clock signal from the data signal.

c) Comparing the recovered slave clock signal with a master clock signal that is generated by a master clock in the master component, and generating a clock control signal that is associated to the result of this comparison.

d) Adjusting, based on the clock control signal, the slave clock in the slave component to the master clock.

The data communication system and the method are different realizations of the same inventive concept. Explanations and definitions provided for one of these realizations are therefore valid for the other realization, too.

In high-speed data communication (typically taking place with 100 Mbps or higher), there is a need to have accurate knowledge about the actual clock frequency. This can be done by using accurate clocks (e.g. crystal clocks on two sides), or there is a need to be able to track the non-accurate clock frequency. An important advantage of the proposed data communication system and method is that the data arrives at a frequency that is "prescribed" by the master (e.g. an important system clock frequency), without the need to have an accurate clock at the slave side (the side which is restricted in space and power). Accordingly, the slave clock can be realized with small components having a low power consumption.

In the following, various preferred embodiments of the invention will be described that relate to the data communication system and the method described above.

According to a first preferred embodiment, the slave clock comprises or completely consists of a voltage controlled oscillator (VCO) or current controlled oscillator (CCO). A VCO and a CCO are components known to persons skilled in the art that allow for an adjustment of their output frequency by an external control voltage or current, respectively.

In general, the link between the slave component and the master component may be any kind of communication channel that can carry the data signal and the clock control signal. If the data signal and/or the clock control signal are for example realized by wireless (RF) signals or optical signals, the link may simply be a medium in which these signals can propagate. If the data signal and the clock control signal are realized by different modalities, the link will comprise carriers for both of them.

In a preferred embodiment, the link comprises (at least) two signal wires via which electrical signals can be changed between the slave component and the master component. In this case the data signal and/or the clock control signal can for example be represented by voltages or currents applied to said signal wires. Most preferably, the link consists of just two signal wires that can carry the data signal and/or the clock control signal. Realizing the link by just two signal wires minimizes the space requirements while simultaneously guaranteeing a reliable connection.

The master component may optionally comprise a transmitter for transmitting a (preferably digital) signal via the link, said signal being called "master signal" in the following. Additional data and/or control commands (besides the clock control signal) can be communicated from the master component to the slave component by this master signal, wherein this communication advantageously uses the available link.

The slave component preferably comprises a receiver for receiving an "additional signal" (besides the clock control signal) via the link. This additional signal may particularly be the master signal of the aforementioned embodiment that is generated by the master component.

According to a preferred embodiment of the invention, the data signal, the clock control signal, the master signal, and/or the additional signal is represented by the difference in a voltage and/or a current between two signal wires of the link (for example as the difference (V1−V2) if V1 and V2 are the voltages on said two signal wires). The sign (polarity) of this difference may then for example represent the "0" and "1" bits of the respective signal.

According to another embodiment, the data signal is represented by the variation of a load that is coupled in the slave component to two signal wires of the link. This load variation can then be sensed by a receiver in the master component.

The clock control signal, the additional signal, and/or the master signal is preferably represented by a common mode voltage and/or current on two signal wires of the link (for example as the value (V1+V2)/2 if V1, V2 are the voltages on said two signal wires). This representation can favorably be combined with the above mentioned embodiment in which the data signal is represented by the difference between a voltage and/or a current because it allows that the same two signal wires are used for the communication of the data signal and the clock control signal (and/or master signal, additional signal). The representation of these signals could (theoretically) also be reverse (i.e. the data signal could be common mode and the clock control signal differential). Representation of the data signal as a difference is however preferred because this typically requires a higher transmission rate.

According to another embodiment of the invention, the master signal (or the "additional signal") overrides the data signal. For example, if both the data signal and the master signal are represented as a difference between currents or voltages on two signal wires of the link, the difference imposed by the master signal may be so large that its sign (polarity) is not changed by the simultaneous data signal. Accordingly, information encoded in said sign (polarity) of the master signal can be retrieved irrespective of the data signal.

The master component and the slave component are two compatible parts of the data communication system that are specifically designed with respect to each other. An essential part of the invention is realized in each of these components, which are commercial commodities of their own. Accordingly, the invention also relates to a slave component as an element of its own, said slave component comprising:

A controllable slave clock for generating a slave clock signal, wherein said clock can be adjusted by a clock control signal.

A transmitter for transmitting a data signal that is clocked by the slave clock signal.

Similarly, the invention relates to a master component as an element of its own, said master component comprising:

A receiver for receiving a data signal from the aforementioned slave component.

A master clock for generating a master clock signal.

A clock controller that receives the master clock signal and the data signal and that generates a clock control signal which can adjust the slave clock of the aforementioned slave component to the master clock.

The invention further relates to a medical instrument, particularly an interventional instrument like a catheter or a guide-wire, said instrument comprising a slave component of the kind described above. An advantage of this medical instrument is that it can be miniaturized due to the low space requirements of the slave component while it allows at the same time for a high-speed data transmission to external equipment.

Finally, the invention relates to a medical system that comprises the aforementioned instrument and external equipment with a master component, wherein the slave component of the instrument and said master component are compatible (i.e. form a data communication system according to the invention) and are coupled via a link, for example a cable.

BRIEF DESCRIPTION OF THE DRAWINGS

These and other aspects of the invention will be apparent from and elucidated with reference to the embodiments described hereinafter.

In the drawings.

Like reference numbers or numbers differing by integer multiples of 100 refer in the Figures to identical or similar components.

DETAILED DESCRIPTION OF EMBODIMENTS

Diagnosis and treatment in minimally invasive healthcare procedures may be improved by integrating imaging and sensing devices at the tip of interventional instruments—such as catheters and guide-wires. However, the very limited size of these instruments poses an important challenge in integrating the required functionality. Micro-machining (MEMS) sensors can be integrated with ASIC technology and enable advanced imaging and/or sensing functionality in a very small area. The related trend is that an increasing amount of data needs to be transferred from the tip of the instrument to the external equipment.

Communication between the devices at the tip of an instrument (in-vivo) and the external equipment (ex-vivo) requires a link that is capable of transferring data in an effective way. In this context "effective" refers to: causing little in-vivo power dissipation, requiring simple and small in-vivo functionality, and requiring a low number of signal wires to connect the in-vivo and the ex-vivo functionality.

A low wire-count is important due to the limited space available to route the wires. The lumen of a guide-wire typically is 250 μm while the diameter of a catheter is 1-5 mm (with a trend towards smaller catheters). This also restricts the available area for in-vivo functionality. The in-vivo power dissipation is important because of safety regulations on heating human tissue.

Realization of a robust (bi-directional) high speed serial link between two cable ends typically requires:
One or two transmitter(s) that send data at a defined speed.
One or two receivers(s) that receive data at the intended speed.
Two signal wires that allow transferring high speed signals in a differential way.
One or two reference clock devices.

Figure 1:
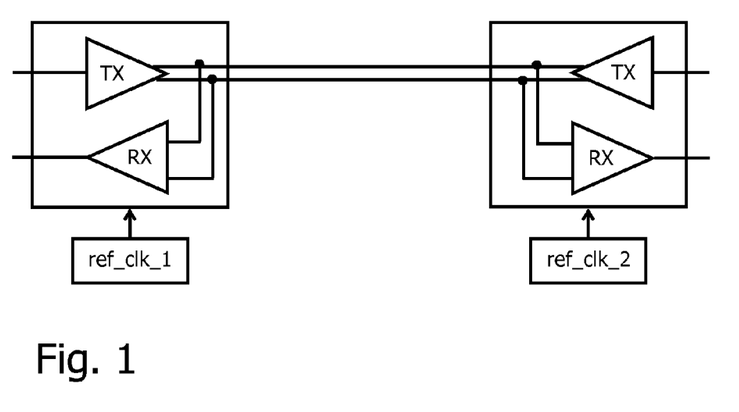
FIG. 1 illustrates a data communication with reference clocks in both the slave and the master.

FIG. 1 shows schematically a data communication with two clock devices, one device (ref_clk_1) being located at the master site and one device (ref_clk_2) being located at the slave site. Typically, there are strict requirements on clock jitter and clock frequency matching in this case.

Figure 2:
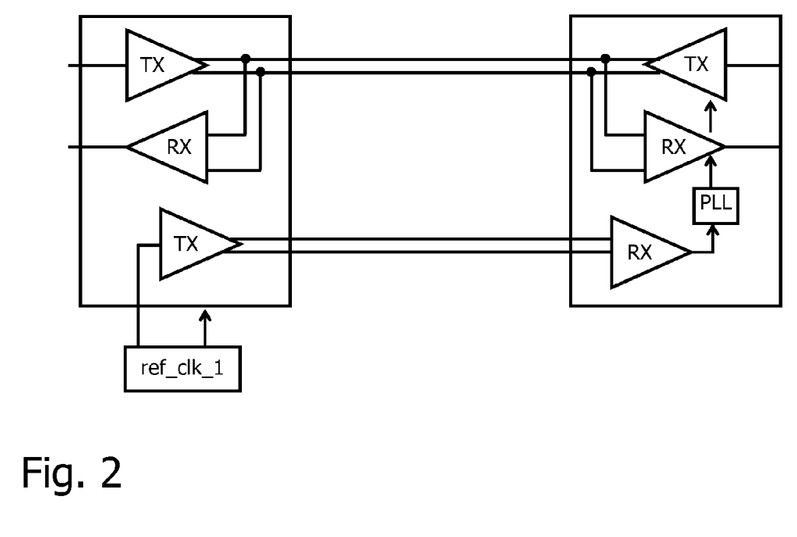
FIG. 2 illustrates a data communication in which a clock signal of a master clock is transmitted to a slave.

FIG. 2 shows schematically a data communication in which there is only one reference clock (ref_clk_1) at the master site. As this clock is not located near the (active) transmitter of the slave, extra circuitry (e.g. receiver circuitry and PLL) and extra wire(s) are needed to transfer the clock signal from the master to the slave site of the link.

In case of catheter or guide-wire applications, most of the high-speed dataflow is from the devices at the tip (slave, "in-vivo") to external equipment (master, "ex-vivo"). Transmitting high-speed (HS) data from slave to master at the required speed typically requires an accurate reference clock (e.g. a crystal oscillator) at the slave or transport of an accurate clock signal via one or two wires towards the slave. Due to the limited area available, it is not attractive to implement a crystal in-vivo in order to generate a reference clock signal (FIG. 1). For the same reason, the transport of an accurate clock signal (FIG. 2) is not attractive due to the need of additional wire(s), hardware and power dissipation.

The present invention proposes a solution that is capable of sending data from slave to master at a defined speed without the need of such accurate clock reference at the slave. The solution requires only two signal wires and the functional partitioning is such that most functionality and power dissipation is "ex-vivo". Full control of the link remains "ex-vivo".

Figure 3:
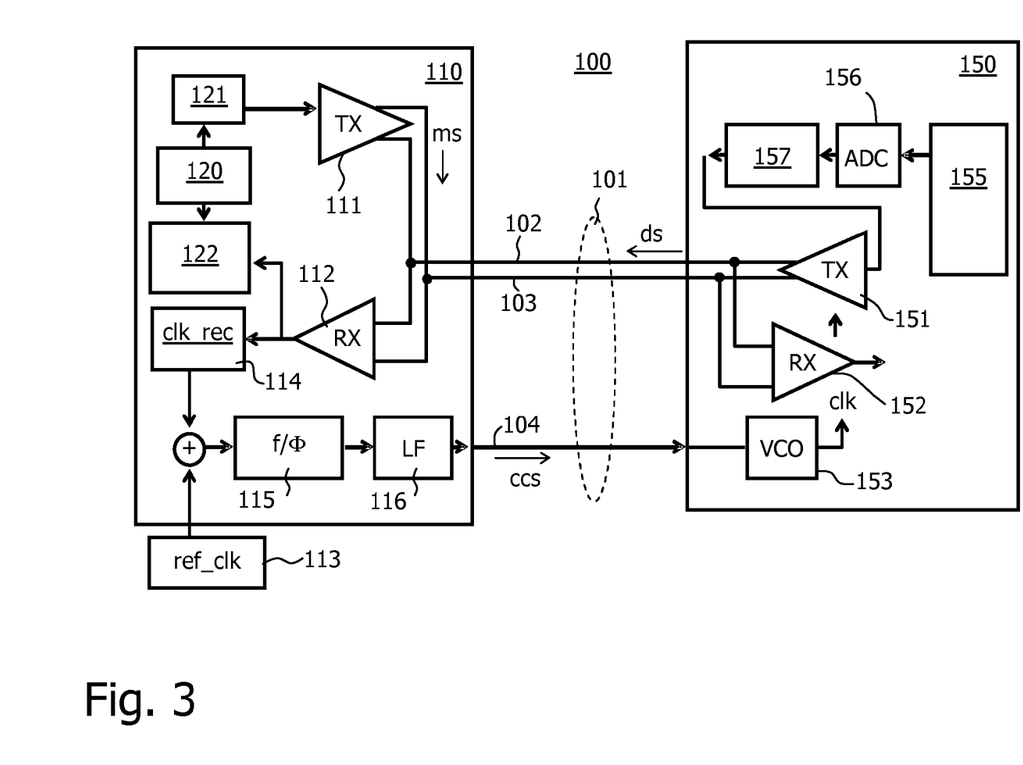
FIG. 3 illustrates schematically a communication system according to the present invention.

FIG. 3 shows a block diagram of a data communication system 100 according to an embodiment of the present invention. The system 100 comprises three main components, namely:
A "slave component" 150 on the "in-vivo" side that delivers most data, but contains simple data link functionality and consumes little power.
A "master component" 110 on the "ex-vivo" side that has full control over the link, contains more complex functionality, and consumes more power.
A link 101 connecting them, for example a cable or other type of inter-connect.

The slave component 150 may for example be integrated into a smart guide-wire or a catheter that is equipped with sensors, actuators and/or imaging devices at the tip, which are schematically represented by a box 155. The gathered (analogue) signals will be converted into digital data e.g. by means of a sigma-delta ADC 156. The data is encoded in an encoder 157 and sent by a transmitter 151 as a "data signal" ds over the link 101 to the ex-vivo world.

The cable 101 preferably comprises two signal wires 102 and 103 (a third connection 104 is only shown to illustrate the separate signal flow). As will be explained in more detail below, these signal wires 102 and 103 transfer the high-speed data signal ds (via differential signaling), a VCO clock control signal ccs (via common-mode signaling), and additional control and/or low-speed data (via differential or common-mode signaling). Besides the two signal wires (or "functional wires"), the cable 101 may in practice additionally comprise extra connections (not shown) for power supply (VDD, GND), yielding a total of four wires (in case of a full electrical link). If a battery would be supplied to the slave component 150, it might be possible to limit the total number of wires to two.

The in-vivo slave component 150 contains a "slave clock", here realized by a voltage controlled oscillator (VCO) 153 that delivers a "slave clock signal" clk to the local high-speed transmitter 151 and receiver 152. The speed depends on the application but the effective data rate could be hundreds of Mbit/s. The high-speed transmitter 151 can be an active transmitter (FIG. 4) or a load modulating device (FIG. 5). As the latter one will give less in-vivo dissipation, it might be preferred. The in-vivo receiver 152 must be capable of determining the polarity of the differential input signal. The speed of the receiver depends on the application, but will be moderate in most cases.

The ex-vivo master component 110 comprises a high-speed receiver 112 for receiving the data signal ds sent by the in-vivo slave component 150. Moreover, the master component 110 is the master of the communication. It controls the slave data rate and the mode of operation of both master and slave. To be able to control the HS-data rate, the master component 110 comprises a "clock controller" with the following components:
means 114 to do clock recovery,
a frequency- and/or phase-detector 115 to compare the frequency of the recovered slave clock signal and the reference clock frequency of a master clock signal ref_clk provided by a master clock 113, a loop-filter 116.

The master component 110 also contains means 122 to do data recovery and data decoding. Data recovery is possible by means of oversampling techniques or by means of an (extra) PLL that locks on the incoming data.

Furthermore, the master component 110 contains a control unit 120 that is capable of sending low speed data (storage 121) or control bits as a "master signal" ms via a transmitter 111 to the slave 150. Said transmitter 111 may also provide energy (a fixed current) to the in-vivo transmitter 151 in case of a passive in-vivo HS-transmitter.

The VCO 153 may be realized in an ASIC at the tip of the corresponding instrument (e.g. guide-wire or catheter). This non-accurate clock source generates a clock signal clk, using only a low amount of power and requiring a limited amount of space. As described above, this signal clocks the local transmitter 151 and receiver 152. The in-vivo transmitter 151 sends encoded HS-data as a data signal ds across the link 101, wherein the encoding is such that the clock frequency can be retrieved from this transmitted signal. The ex-vivo master component 110 receives the data signal ds, performs the clock recovery, after which the clock frequency is compared with a reference clock frequency ref_clk. By means of a negative feedback loop, the frequency of the VCO is regulated to fit the reference clock frequency.

Furthermore, it is possible to combine the HS-data ds and the VCO clock control signal ccs (and optionally also a master signal ms provided by the in-vivo transmitter 111) across the same two signal wires 102 and 103: HS-data ds can be driven differentially, using a small signal swing. The VCO clock control voltage ccs is transferred via the common-mode (CM) voltage level of the signal wires. This approach will be explained in more detail below with reference to FIGS. 4 and 5.

Figure 4:
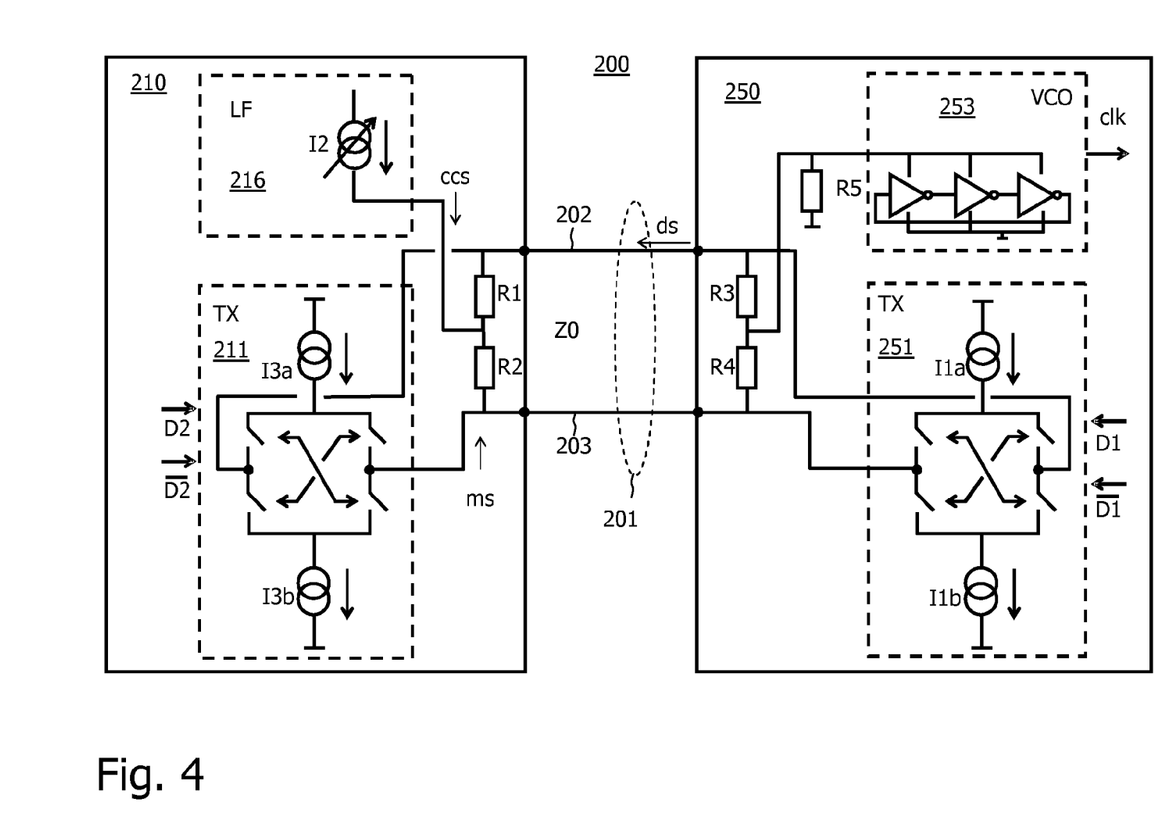
FIG. 4 schematically illustrates a particular embodiment of the data communication system in which data signals are represented by current differences.
Figure 5:
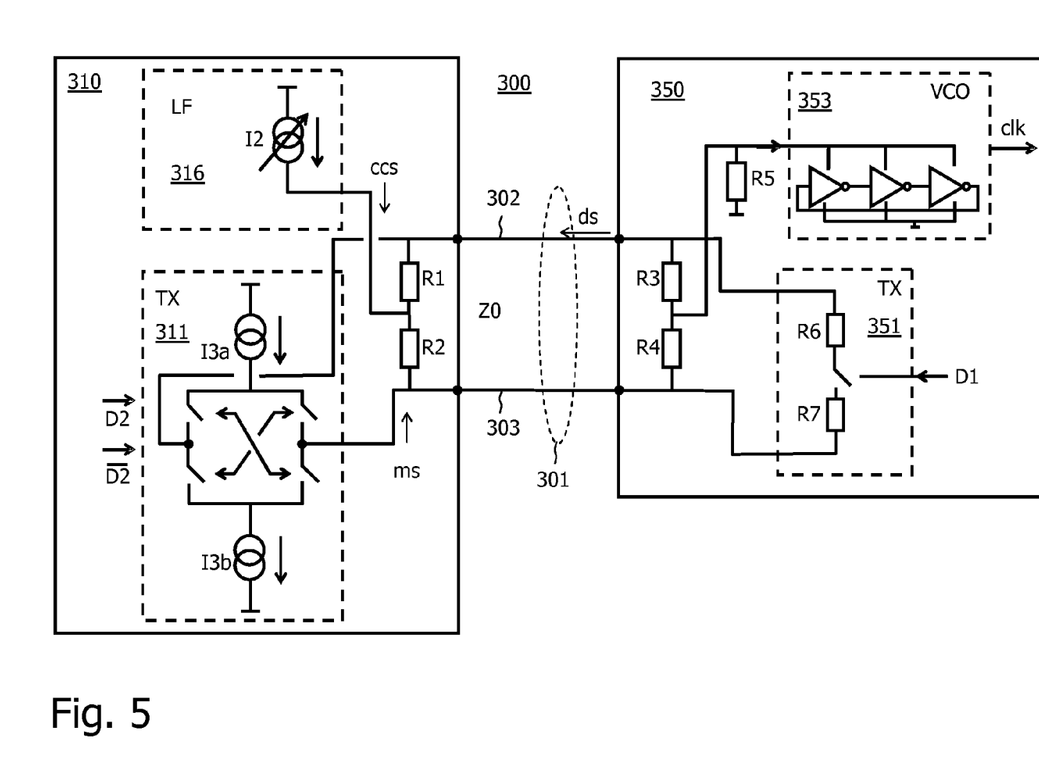
FIG. 5 schematically illustrates a particular embodiment of the data communication system in which data signals are represented by load variations.

FIG. 4 shows a block diagram of a communication system 200 with a master component 210 and a slave component 250 that are generally designed as shown in FIG. 3. Particular components of this system are shown in more detail to illustrate a possible implementation of a two signal wire interface (as explained above, there are typically extra wires for power supply that will not be considered in the following).

Due to the typical length of the cable wiring of the link 201 (±2 m) and the typical speed of the data-link (>>10 MHz), the cable behaves as a transmission line. Therefore, the characteristic impedance (Z0) of the cable is important and matched termination resistors R1, R2, R3, R4 on termination and/or transmission side need to be placed to minimize undesirable reflections.

During high-speed transmission, the in-vivo high speed transmitter 251 transmits gathered data (D1). The HS-signal ds uses differential signaling to minimize electromagnetic radiation (EMI) and susceptibility (EMS). The shown implementation of the transmitter 251 runs at a fixed bias current (I1a and I1b), which minimizes disturbance of the local supply voltage. A data bit D1="1" may for example be encoded by connecting a first current source I1a to a first signal wire 202 and a second current source I1b to the other signal wire 203, while a data bit D1="0" is encoded by connecting the first current source I1a to the second signal wire 203 and the second current source I1b to the first signal wire 202. During high-speed transmission mode, the ex-vivo low-speed transmitter 211 maybe turned off.

The loop filter 216 in the master component 210 is a part of the negative feedback loop that will regulate the frequency of the VCO 253 in the slave 250 to the required value. In the shown implementation, the loop-filter output delivers a regulated current I2, which is translated (by a resistor R5) into a common mode (CM) voltage in the close vicinity of the VCO 253.

The ex-vivo master component 210 is capable of overruling the HS-data-stream ds by activating its transmitter 211 and driving low-speed (or medium speed) data D2 or control data as a "master signal" ms across the link 201. By choosing the ex-vivo bias currents (I3a and I3b) larger than the in-vivo currents (I1a and I1b), the in-vivo receiver (not shown) can detect the ex-vivo data signal ms by sensing the polarity of the differential signal. During low speed data-transmit mode of the master signal ms, the in-vivo HS-transmitter 251 preferably remains active. This allows the frequency control loop to remain active and to keep lock between the reference clock and the in-vivo clock.

FIG. 5 shows a block diagram of a communication system 300 with a master component 310 and a slave component 350 that are generally designed as shown in FIG. 3. Particular components of this system are shown in more detail to illustrate an alternative implementation of the high-speed transmitter.

In this version, the in-vivo HS-transmitter 351 has been implemented as a load modulating device. During HS-transmit of a data signal ds, the ex-vivo LS-transmitter 311 delivers a fixed differential current. Resistors R1 and R2 in the master component 210 provide a matched termination at the ex-vivo side. The termination at the in-vivo site comprises the resistors R3 and R4, to which the resistors R6 and R7 can optionally be coupled in parallel by the HS-transmitter 351. Thus the termination can be switched between a value larger than the characteristic impedance (e.g 5·Z0) and a value lower than the characteristic impedance (e.g. 0.5·Z0). This switching, which represents the HS-data D1, will cause reflections (constituting the data signal ds). As the reflections are the only HS-information happening on the link 301, they can be detected rather easily.

The ex-vivo transmitter 311 can send data D2 as a master signal ms across the link 301 by toggling the polarity of the (fixed) current of the low-speed transmitter 351. The low-speed data ms can be sensed by the in-vivo receiver (not shown) by sensing the polarity of the differential signal.

Figure 6:
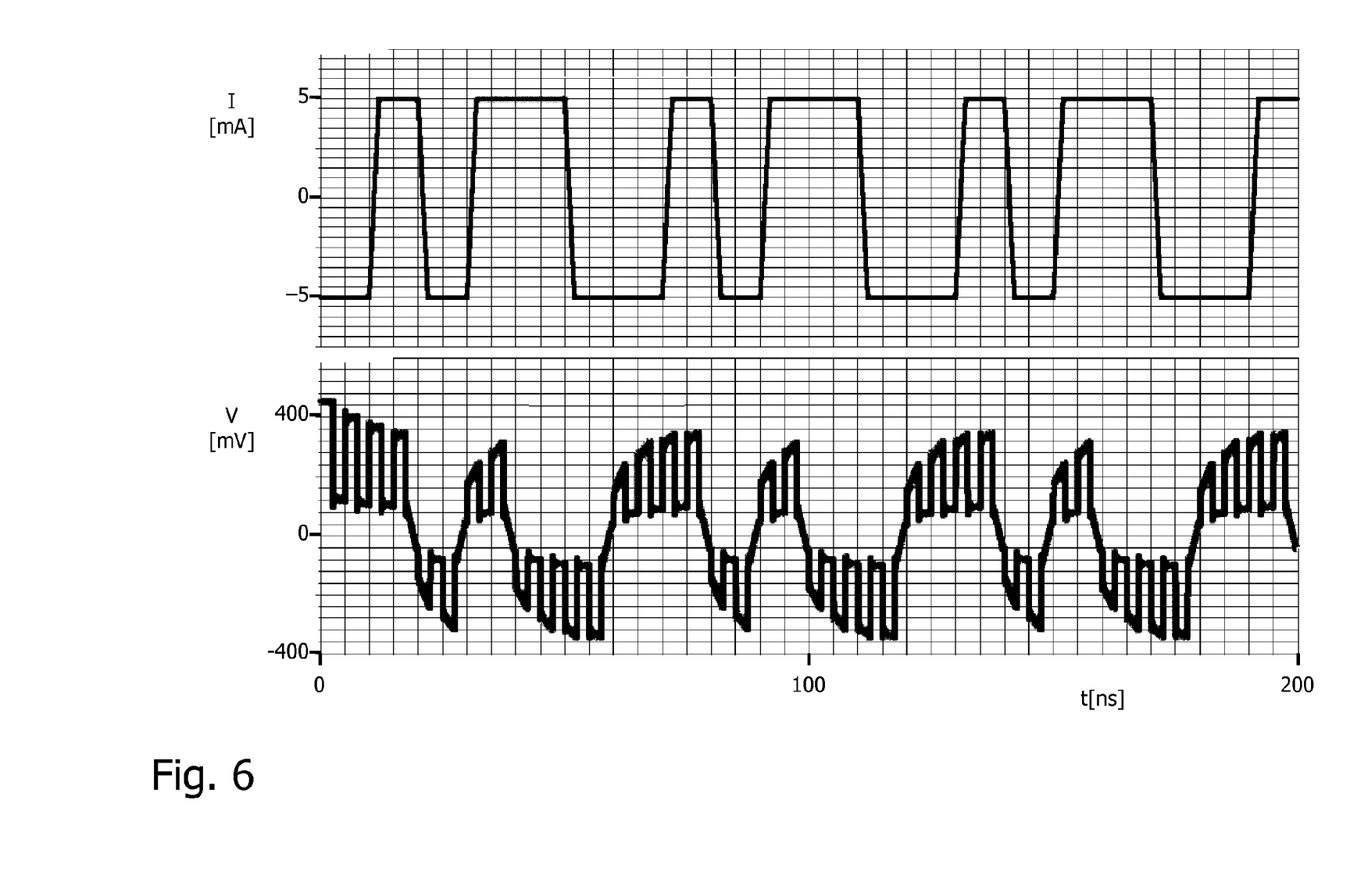
FIG. 6 shows exemplary courses of the voltage and current on the link of the data communication system of FIG. 5.

The data bit ("1" or "0") can be encoded in the master signal ms in many ways, for example by varying the duration of the inverse polarity pulse. FIG. 6 shows an example of such pulse width modulation, wherein the upper curve represents the current I flowing in a signal wire 302 of the link and the lower diagram shows the voltage between the signal wires 302 and 303 of the link. In this example, the HS-transmitter 351 sends a fixed clock (no data contents) at a clock rate of 200 Mbit/s. The low-speed data rate is a factor of 12 lower. The long pulses can be distinguished from the short pulses by clocking the (polarity of the) voltage signal with the in-vivo clock 353. The duration of the inverse polarity pulses (I=−5 mA) determines the value of the transmitted data bits. Accordingly, the shown low speed master signal is a (010101) sequence.

It should be noted that the HS-data encoding in the data signal ds is an important aspect of the proposed systems. The data encoding must allow clock recovery under all conditions. Clock recovery is required to be able to regulate the HS-data rate. Clock recovery is possible by counting the number of transitions in the HS-data signal (frequency detection) or by comparing the position of the HS-data transitions and the reference clock transitions (phase comparison) or by a mix of these two methods. At start-up, frequency detection works best as it cannot cause false locks while phase detection can. The disadvantage of frequency detection is that it requires a fixed/known amount of transitions in the HS-data signal; this can be arranged in the encoding of the data or can be guaranteed by sending a fixed/known data pattern at the start of a data sequence.

Furthermore, HS-data encoding is important as the in-vivo clock signal may suffer from jitter due to electrical disturbances on the VCO control signal. By choosing a type of data encoding with a strong clock frequency component, the data recovery will suffer less from this jitter.

A basic data encoding could be the well known Manchester coding (i.e. "0" and "1" are expressed by a transition between low and high at the midpoint of a fixed period). The efficiency of the Manchester coding is rather low (many transitions, high bandwidth needed for data transfer). Furthermore, Manchester does not foresee a word-sync or frame-sync, this probably needs to be added on top the Manchester coding. 8 bit-to-10 bit encoding could therefore be an alternative (cf. U.S. Pat. No. 4,486,739).

In summary, an electrical high speed serial link was described that is capable of transferring data from devices at the tip of an interventional instrument (in-vivo) to the external equipment (ex-vivo) in a power efficient and area effective way. The ability to transfer the high-speed data from the tip at a defined speed is achieved without the need of an accurate in-vivo clock reference source. Only two signal wires are required, and the functional partitioning is such that most of the functionality and power dissipation is ex-vivo. Full control of the link remains ex-vivo. All these aspects allow for large amounts of data being transferred in a highly miniaturized solution.

The system according to the invention avoids the need of an accurate reference clock signal at the slave side. Instead, a control signal is needed. An important aspect in this respect is that it is easier to transfer a low-frequency control signal (potentially via multiplexing) than a high speed clock signal (especially in a catheter or guide-wire). High speed signals are difficult to multiplex and often require multiple signal wires if done in the electrical domain (coax like cable or twisted pair etc). The same holds for receiving the signals; it is easier to receive a low-frequency control signal than a high speed clock signal.

Accordingly, the approach of the invention implies the use of one high-speed data signal and one low frequency control signal. In general, the high-speed data signal could be transferred via (two) electrical signal wires, via a single optical wire, or wirelessly. The control signal could be transferred in multiple ways, but due to the low-frequency contents of this signal it is not attractive to do it wirelessly or optically (assumed that the system will contain electrical signals). If there are no electrical wires (e.g. for MRI compatibility reasons), of course also the control signal needs to be transferred optically or wirelessly.

The proposed solution is especially useful in communication links with minimally invasive instrumentation that require high-speed data transport , e.g. ultrasound imaging from a catheter or guide-wire, such as intravascular ultrasound (IVUS), intra-cardiac echography (ICE), forward-looking IVUS/ICE, ultrasound-based ablation monitoring, but also all types of in-body sensors (flow, pressure, temperature) etc.

In-body sensors do not really require a high-speed link. Speeds of sensors are limitated to e.g. 1 MHz. while all kind of imaging easily requires hundreds of Mb/s.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A medical system, comprising:
   a) an interventional instrument including a slave component further including:
      a1) a controlled oscillator for generating a slave clock signal in response to a received clock control signal via a link, and
      a2) a transmitter for transmitting a data signal that is clocked by the slave clock signal on the link, the data signal includes encoded data from sensors, actuators, or imaging devices; and
   b) external equipment including a master component further including:
      b1) a receiver for receiving said data signal via the link,
      b2) a master clock unit for generating a master clock signal, and
      b3) a clock controller being configured to i) receive the master clock signal and the data signal, ii) recover the slave clock signal from the received data signal, and iii) compare the frequency of the recovered slave clock signal and the master in order to generate the clock control signal for adjusting the controlled oscillator to the master clock unit,
      b4) a transmitter for transmitting at least the clock control signal via the link; and
   c) the link includes at least two wires.

2. The system according to claim 1, wherein the controlled oscillator is a voltage controlled oscillator or current controlled oscillator.

3. The system according to claim 1, wherein the link includes two signal wires.

4. The system according to claim 1, wherein the transmitter of the master component transmits a master signal via the link.

5. The system according to claim 4, wherein the master signal overrides the data signal.

6. The system according to claim 1, wherein the slave component includes a receiver for receiving an additional signal from the link.

7. The system according to claim 1, wherein at least one of the data signal, the clock control signal, a master signal, and an additional signal is represented by a difference of a voltage and/or a current between two signal wires of the link.

8. The system according to claim 7, wherein the clock control signal is represented by a common mode voltage and/or current on two signal wires of the link.

9. The system according to claim 1, wherein the data signal is represented by the variation of a load coupled in the slave component to two signal wires of the link.

10. The system according to claim 9, wherein the clock control signal is represented by a common mode voltage and/or current on two signal wires of the link.

11. The system according to claim 1, wherein the data signal, the clock control signal, and/or the master signal is represented by a common mode voltage and/or current on two signal wires of the link.

12. The system according to claim 1, wherein the interventional instrument is a guidewire.

13. The system according to claim 1, wherein the interventional instrument is a catheter.

* * * * *